US00PP12181P2

(12) United States Plant Patent
Miyazaki

(10) Patent No.: US PP12,181 P2
(45) Date of Patent: Oct. 30, 2001

(54) SENECIO GENUS PLANT NAMED 'SUNSENEDIBU'

(75) Inventor: Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/345,511

(22) Filed: Jul. 1, 1999

(51) Int. Cl.[7] ..... A01H 5/00
(52) U.S. Cl. ..... Plt./263
(58) Field of Search ..... Plt./263

(56) References Cited

PUBLICATIONS

Asteraceae Cladistics & Classifications, K. Bremer, 1994, p. 508.*

* cited by examiner

*Primary Examiner*—Bruce R. Campell
*Assistant Examiner*—Anne Marie Grünberg
(74) *Attorney, Agent, or Firm*—Burns, Doane, Swecker & Mathis, L.L.P.

(57) ABSTRACT

Disclosed herein is a Senecio genus plant named 'Sunsenedibu' which is tall and dome-shaped with abundant branching. There are very few pubescenes on its stems. The leaf is shorter and narrower than that of other *Senecio L.* 'Sunsenedibu' has no stipule. 'Sunsenedibu' has large flower clusters with large flowers. The flowers is single flowered and has no marginal variegation. The color of the petal and the disk flower is deep violet. The blooming period is early and blooming term is longer than *Senecio cruentus*. Flower buds grow one after another from axil. 'Sunsenedibu' has low fertility.

2 Drawing Sheets

BACKGROUND OF THE VARIETY

The present invention relates to a new and distinct variety of Senecio genus plant named 'Sunsenedibu'. 'Sunsenedibu' is a distinct and unique variety, which is a dome-shaped plant of high height with abundant branching, deep violet flowers, and long blooming term.

There are many varieties of *Senecio L. Senecio cruentus* is well known as Cineraria and cultivated in the world. There are many cultivated varieties having flowers of a single color of white, pink red, blue or violet. Some varieties have marginal variegation with off color parts.

The female parent used in the crossing of 'Sunsenedibu' is a cultivar, *Senecio cruentus*, 'Jupiter Blue' (not patented in the United States). 'Jupiter Blue' is a compact dome-shaped plant, 18.5 cm high. The stem is thick, 8.3 mm in diameter, with anthocyanin coloration. The leaf is of a serrated heart form and grayish yellow green having a medium size, 12.0 cm long and 12.5 cm wide. The flower is single flowered and has vivid blue petals with deep blue disk flowers and no marginal variegation. 'Jupiter Blue' has some scent.

The pollen parent used in the crossing of 'Sunsenedibu' is *Senecio heritierii* (not patented in the United States), which was introduced from nurseries in England. *Senecio heritierii* is a high and dome-shaped plant, 26 cm high abundant branching. The stem is 5.1 mm in diameter, with no anthocyanin coloration. The leaf is of a serrated heart form and light yellowish green. Leaf size is small, 5.5 cm long and 6.3 cm wide. The flower is single flowered, having strong purple petals with vague white parts and strong reddish purple disk flowers. *Senecio heritierii* has no scent.

Controlled crossing with *Senecio cruentus* 'Jupiter Blue' and *Senecio heritierii* was conducted at Hakushu-cho, Kitakoma-gun, Yamanashi-ken, Japan in January 1995. Seedlings from this crossing were grown since July 1995. One variety was selected in January 1996 among them in view of flower color and early blooming. After multiplication by tissue culture, the botanical characteristics of the selected variety were examined and tested in potting, using parent varieties, as well as 'Miss Yokohama', and 'Midget', for comparison since July 1996. As a result, it is confirmed that this selected variety met our criteria of being uniform and stable in its characteristics.

Then this new variety of Senecio genus plant was named 'Sunsenedibu' (*Senecio cruentus*×*Senecio heritierii*).

*Senecio cruentus* 'Jupiter Blue' and *Senecio heritierii* are presently maintained at Hakushu-cho, Kitakoma-gun, Yamanashi-ken, Japan.

In the following descriptions, the color-coding is in accordance with The Horticultural Colour Chart of The Royal Horticultural Society, London, England (R.H.S. Colour Chart), and a color chart based on The Japan Color Standard for Horticultural Plant (J.H.S. Color Chart).

The botanical characteristics of the female parent plant *Senecio cruentus*, 'Jupiter Blue' used in the crossing of 'Sunsenedibu' are as follows.

Plant:
- *Growth habit.*—Dwarf compact.
- *Height.*—18.5 cm.

Stem:
- *Thickness.*—8.3 mm.
- *Color.*—Moderate yellowish green (R.H.S.C.C.No. 139C, J.H.S.C.C.No. 3709).
- *Anthocyanin coloration.*—Present.

*Degree of anthocyanin coloration.*—Medium.
*Branching.*—Few.
*Type of primary lateral shoot.*—Branch from every node.
*Pubescence.*—Sparse.
*Length of internode.*—0.5 cm.

Leaf:
*Whole shape.*—Heart form with a swollen basal part, which is notched at where the basal part attaches to a petiole.
*Depth of concavity of leaf margin.*—Shallow.
*Type of convexity.*—Rounded.
*Apex shape.*—Obtuse.
*Base shape.*—Cordate.
*Degree of Undulation.*—Fair.
*Length.*—12.0 cm.
*Width.*—12.5 cm.
*Diameter of petiole.*—5.8 mm.
*Length of petiole.*—6.0 cm.
*Stipule.*—Absent.
*Color of upper surface.*—Grayish yellow green (R.H.S.C.C.No. 38B, J.H.S.C.C.No. 3715).
*Color of reverse surface.*—Moderate yellow green (R.H.S.C.C.No. 138D, J.H.S.C.C.No. 3702).
*Anthocyanin coloration of reverse surface.*—Present.
*Degree of anthocyanin coloration.*—Medium.
*Pubescence of upper surface.*—Present.
*Pubescence of reverse surface.*—Dense.
*Color of pubescence of reverse surface.*—White.

Flower (single-flowered):
*Shape of flower cluster.*—Flat.
*Diameter of flower cluster.*—20 cm. Height of flower cluster.—10 cm.
*Transected shape of corolla.*—Reflex.
*Diameter of flower.*—5.6 cm.
*Size of disk flower.*—1.8 cm.
*Color of petal.*—Vivid blue (R.H.S.C.C.No. 100A, J.H.S.C.C.No. 7605).
*Marginal variegation.*—Absent.
*Color of disk flower.*—Deep blue (R.H.S.C.C.No. 99B, J.H.S.C.C.No. 7606).
*Petal length.*—1.9 cm.
*Petal width.*—1.0 cm.
*Shape of petal.*—Rectangular.
*Lengthwise warp of petal.*—Convex.
*Concavity of petal tip.*—Present.
*Shape of petal tip.*—Flat.
*Number of ray flower.*—13.
*Number of disk flower.*—110.
*Diameter of pedicel of the first flower in a blooming period* (*the flower is attached to the top of a main stem*).—1.6 mm.
*Length of pedicel of the irst flower in a blooming period* (*the flower is attached to the top of a main stem*).—2.5 cm.
*Number of flowers per flower cluster.*—63.
*Scent.*—Present.

Calyx:
*Degree of concavity.*—Concave.
*Degree of recurvature.*—2.5 mm.
*Color.*—Very pale green (R.H.S.C.C.No. 130D, J.H.S.C.C.No. 4302).
*Anthocyanin coloration.—Absent.*

Pistil:
*Color.*—Deep blue (R.H.S.C.C.No. 99B, J.H.S.C.C.No. 7606).
*Number.*—1.
*Type.*—The top of the style is separated into two and the shape of the top is truncated.

Stamen:
*Color.*—Deep blue (R.H.S.C.C.No. 99B, J.H.S.C.C.No. 7606).
*Type.*—5 anthers are connate, with separated filaments.
*Blooming period.*—December (Sowing in August).

Hardiness:
*Cold.*—Good.
*Heat.*—Good.

Resistance:
*Disease.*—Good.
*Insect.*—Good.

The botanical characteristics of the male parent plant *Senecio heritierii* used in the crossing of 'Sunsenedibu' are as follows.

Plant:
*Growth habit.*—Semi-dwarf erect.
*Height.*—26 cm.

Stem:
*Thickness.*—5.1 mm.
*Color.*—Very pale green (R.H.S.C.C.No. 128D, J.H.S.C.C.No. 4902).
*Anthocyanin coloration.*—Absent.
*Branching.*—Abundant.
*Type of primary lateral shoot.*—Branch from every node.
*Pubescence.*—Dense.
*Length of internode.*—0.8 cm.

Leaf:
*Whole shape.*—Heart form with a swollen basal part, which is notched at where the basal part attaches to a petiole.
*Depth of concavity of leaf margin.*—Medium.
*Type of convexity.*—Acute.
*Apex shape.*—Obtuse.
*Base shape.*—Cordate.
*Degree of undulation.*—Weak.
*Length.*—5.5 cm.
*Width.*—6.3 cm.
*Diameter of petiole.*—3.5 mm.
*Length of petiole.*—7.5 cm.
*Stipule.*—Absent.
*Color of upper surface.*—Light yellowish green (R.H.S.C.C.No. 136D, J.H.S.C.C.No. 4002).
*Color of reverse surface.*—Very pale green (R.H.S.C.C.No. 128D, J.H.S.C.C.No. 4902).
*Anthocyanin coloration of reverse surface.*—Absent.
*Pubescence of upper surface.*—Dense.
*Pubescence of reverse surface.*—Dense.
*Color of pubescence of reverse surface.*—White.

Flower (single flowered):
*Shape of flower cluster.*—Uneven.
*Diameter of flower cluster.*—18 cm.
*Height of flower cluster.*—15 cm.
*Transected shape of corolla.*—Flat.
*Diameter of flower.*—4.8 cm.
*Size of disk flower.*—0.9 cm.
*Color of petal.*—Strong purple (R.H.S.C.C.No. 81B, J.H.S.C.C.No. 8605).
*Marginal variegation.*—Present.
*Diameter of off color part.*—1.3 cm.
*Border of marginal variegation.*—Vague.

*Color of disk flower.*—Strong reddish purple (R.H.S.C.C.No. 72A, J.H.S.C.C.No. 9214).
*Petal length.*—2.2 cm.
*Petal width.*—0.4 cm.
*Shape of petal.*—Rectangular.
*Lengthwise warp of petal.*—Flat.
*Concavity of petal tip.*—Present.
*Shape of petal tip.*—Acute.
*Number of ray flower.*—13.
*Number of disk flower.*—110.
*Diameter of pedicel of the first flower in a blooming period (the flower is attached to the top of a main stem).*—1.2 mm.
*Length of pedicel of the first flower in a blooming period (the flower is attached to the top of a main stem).*—2.5 cm.
*Number of flowers per a flower cluster.*—35.
*Scent.*—Absent.

Calyx:
*Degree of concavity.*—Flat.
*Degree of recurvature.*—3.1 mm.
*Color.*—Very pale green (R.H.S.C.C.No. 128D, J.H.S.C.C.No. 4902).
*Anthocyanin coloration.*—Present.

Pistil:
*Color.*—Strong reddish purple (R.H.S.C.C.No. 72A, J.H.S.C.C.No. 9214).
*Number.*—1.
*Type.*—The top of the style is separated into two and the shape of the top is truncated.

Stamen:
*Color.*—Strong reddish purple (R.H.S.C.C.No. 72A, J.H.S.C.C.No. 9214).
*Type.*—5 anthers are connate, with separated filaments.
*Blooming period.*—End of January (Sowing in August).

Hardiness:
*Cold.*—Good.
*Heat.*—Good.

Resistance:
*Disease.*—Good.
*Insect.*—Good.

The botanical characteristics of the similar variety 'Miss Yokohama' (note patented in the United States) used for examination as a comparison variety are as follows.

Plant:
*Growth habit.*—Dwarf compact.
*Height.*—19 cm.
*Spread.*—cm.

Stem:
*Thickness.*—5.4 mm.
*Color.*—Moderate yellowish green (R.H.S.C.C.No. 139C, J.H.S.C.C.No. 3709).
*Anthocyanin coloration.*—Present.
*Degree of anthocyanin coloration.*—Medium.
*Branching.*—Fair.
*Type of primary lateral shoot.*—Branch from every node.
*Pubescence.*—Dense.
*Length of internode.*—0.5 cm.

Leaf:
*Whole shape.*—Heart form with a swollen basal part, which is notched at where the basal part attaches to a petiole.
*Depth of concavity of leaf margin.*—Medium.
*Type of convexity.*—Acute.
*Apex shape.*—Medium.
*Base shape.*—Cordate.
*Degree of undulation.*—Weak.
*Length.*—17.5 cm.
*Width.*—13.0 cm.
*Diameter of petiole.*—5.2 mm.
*Length of petiole.*—7.7 cm.
*Stipule.*—Present.
*Color of upper surface.*—Moderate yellow green (R.H.S.C.C.No. 137C, J.H.S.C.C.No. 3712).
*Color of reverse surface.*—Moderate yellow green (R.H.S.C.C.No. 138C, J.H.S.C.C.No. 3709).
*Anthocyanin coloration of reverse surface.*—Present.
*Degree of anthocyanin coloration.*—Medium.
*Pubescence of upper surface.*—Dense.
*Pubescence of reverse surface.*—Dense.
*Color of pubescence of reverse surface.*—White.

Flower (single flowered):
*Shape of flower cluster.*—Rounded.
*Diameter of flower cluster.*—23 cm.
*Height of flower cluster.*—17 cm.
*Transected shape of corolla.*—Flat.
*Diameter of flower.*—4.2 cm.
*Size of disk flower.*—1.1 cm.
*Color of petal.*—Vivid violet (R.H.S.C.C.No. 96A, J.H.S.C.C.No. 8005).
*Marginal variegation.*—Present.
*Diameter of off color part.*—2.5 cm.
*Border of marginal variegation.*—Fairly clear.
*Color of disk flower.*—Deep violet (R.H.S.C.C.No. 93A, J.H.S.C.C.No. 8006).
*Petal length.*—1.6 cm.
*Petal width.*—0.8 cm.
*Shape of petal.*—Rectangular.
*Lengthwise warp of petal.*—Convex.
*Concavity of petal tip.*—Present.
*Shape of petal tip.*—Rounded.
*Number of ray flower.*—13.
*Number of disk flower.*—86.
*Diameter of pedicel of the first flower in a blooming period (the flower is attached to the top of a main stem).*—1.7 mm.
*Length of pedicel of the first flower in a blooming period (the flower is attach to the top of a main stem).*—2.7 cm.
*Number of flowers per a flower cluster.*—90.
*Scent.*—Present.

Calyx:
*Degree of concavity.*—Flat.
*Degree of recurvature.*—1.2 mm.
*Color.*—Very pale green (R.H.S.C.C.No. 130D, J.H.S.C.C.No. 4302).
*Anthocyanin coloration.*—Absent.

Pistil:
*Color.*—Deep violet (R.H.S.C.C.No. 93A, J.H.S.C.C.No. 8006).
*Number.*—1.
*Type.*—The top of the style is separated into two and the shape of the top is truncated.

Stamen:
*Color.*—Deep violet (R.H.S.C.C.No. 93A, J.H.S.C.C.No. 8006).
*Type.*—5 anthers are connate, with separated filaments.
*Blooming period.*—January (Sowing in August).

Hardiness:
*Cold.*—Good.
*Heat.*—Good.
Resistance:
*Disease.*—Good.
*Insect.*—Good.

The botanical characteristics of the similar variety 'Midget' (not patented in the United States) used for examination as a comparison variety are as follows.

Plant:
*Growth habit.*—Dwarf.
*Height.*—14 cm.
Stem:
*Thickness.*—5.6 mm.
*Color.*—Moderate yellowish green (R.H.S.C.C.No. 139C, J.H.S.C.C.No. 3709).
*Anthocyanin coloration.*—Present.
*Degree of anthocyanin coloration.*—Medium.
*Branching.*—Fair.
*Type of primary lateral shoot.*—Branch from every node.
*Pubescence.*—Dense.
*Length of internode.*—0.5 cm.
Leaf:
*Whole shape.*—Heart form with a swollen basal part, which is notched at where the basal part attaches to a petiole.
*Depth of concavity of leaf margin.*—Medium.
*Type of convexity.*—Acute.
*Apex shape.*—Acute.
*Base shape.*—Cordate.
*Degree of undulation.*—Fair.
*Length.*—13.9 cm.
*Width.*—10.3 cm.
*Diameter of petiole.*—4.2 mm.
*Length of petiole.*—4.7 cm.
*Stiple.*—Present.
*Color of upper surface.*—Grayish yellow green (R.H.S.C.C.No. 138A, J.H.S.C.C.No. 3514).
*Color of reverse surface.*—Grayish yellow green (R.H.S.C.C.No. 138B, J.H.S.C.C.No. 3715).
*Anthocyanin coloration of reverse surface.*—Absent.
*Pubescence of upper surface.*—Present.
*Pubescence of reverse surface.*—Dense.
*Color of pubescence of reverse surface.*—White.
Flower (single flowered):
*Shape of flower cluster.*—Flat.
*Diameter of flower cluster.*—22 cm.
*Height of flower cluster.*—8 cm.
*Transected shape of corolla.*—Fairly closed.
*Diameter of flower.*—3.2 cm.
*Size of disk flower.*—0.8 cm.
*Color of petal.*—Vivid reddish purple (R.H.S.C.C.No. 74A, J.H.S.C.C.No. 9207).
*Marginal variegation.*—Absent.
*Color of disk flower.*—Strong reddish purple (R.H.S.C.C.No. 72A, J.H.S.C.C.No. 9209).
*Petal length.*—1.5 cm.
*Petal width.*—0.8 cm.
*Sshape of petal.*—Elliptical.
*Lengthwise warp of petal.*—Flat.
*Concavity of petal tip.*—Present.
*Shape of petal tip.*—Acute.
*Number of ray flower.*—13.
*Number of disk flower.*—86.
*Diameter of pedicel of the first flower in a blooming period (the flower is attached to the top of a main stem).*—1.5 mm.
*Length of pedicel of the first flower in a blooming period (the flower is attached to the top of a main stem).*—2.5 cm.
*Number of flowers per a flower cluster.*—180.
*Scent.*—Present.
Calyx:
*Degree of concavity.*—Flat.
*Degree of recurvature.*—2.2 mm.
*Color.*—Moderate yellow green (R.H.S.C.C.No. 139C, J.H.S.C.C.No. 3709).
*Anthocyanin coloration.*—Absent.
Pistil:
*Color.*—Strong reddish purple (R.H.S.C.C.No. 72A, J.H.S.C.C.No. 9209).
*Number.*—1.
*Type.*—The top of the style is separated into two and the shape of the top is truncated.
Stamen:
*Color.*—Strong reddish purple (R.H.S.C.C. No. 72A, J.H.S.C.C.No. 9209).
*Type.*—5 anthers are connate, with separated filaments.
*Blooming period.*—January (Sowing in August).
Hardiness:
*Cold.*—Good.
*Heat.*—Good.
Resistance:
*Disease.*—Good.
*Insect.*—Good.

SUMMARY OF THE NEW VARIETY

'Sunsenedibu' is a high height and dome-shaped plant averaging 34 cm in height at the blooming period. The new variety branches from every node with abundant branching. The stem is 4.2 mm in diameter, with light anthocyanin coloration and has few pubescences.

The leaf is small, 7.0 cm long and 7.7 cm wide, in the shape of a serrated heart form with a swollen basal part, which is notched at where the basal part attaches to a petiole. The leaf is moderate yellowish green, with no anthocyanin coloration. Pubescence on both sides of the leaf is dense. The petiole is 7.8 cm long and 3.0 mm in diameter.

The new variety has large flower clusters which are tall and uneven (the locations of the individual flowers forming a flower cluster are uneven or not flat). The flower is single flowered with no marginal variegation. The transected shape (i.e. the side view of a sagittal section) of the corolla is reflex (i.e. when the corolla opens, petals are turned over; in other words, the petals are curved downward). The flower diameter is 7.0 cm. Petals are 29 mm long and 0.8 cm wide and their color is deep blue. The disk flower is 12 mm in diameter and its color is also deep violet. One flower has 13 ray flowers and 158 disk flowers. 120 flowers are in a flower cluster. The degree of recurvature of calyx is 1.6 mm. Calyx is concave with some anthocyanin coloration. The pedicel is 5.6 cm long and 0.9 mm in diameter. The flowers have some scent.

The blooming period is early and the blooming term is long. After cutting in July in Hakushu-cho, Kitakoma-gun, Yamanashi-ken, Japan, flowers begin to bloom in the first 10 days of December and blooming continues from December to May under appropriate control. If the temperature is maintained at around 15° C., the individual bloom lasts about two weeks. Flower buds of the new variety grow one after another from an axil. The flower is not self-cleaning because the petals remain attached in a wilt and dry state as the flower fully matures.

The new variety has moderate cold hardiness and resistance to heat. The new variety does not die at a temperature around 0° C. However, when frost occurs, the cells of the new variety can be necrosed resulting in the death of the plant. *Senecio cruentus* usually has a tendency to reduce its growth in a hot season, but the new variety has no problem in growing in the hot season.

The new variety's fertility is low. Generally, varieties having high seed fertility have many seeds per flower. The new variety, however, has no seed or very few seeds. Since no seed is formed, there is a part corresponding to the seed coat and only this seed coat part remains in an immature state. There is no embryo or endosperm within the immature seed coat part.

The new variety of Senecio genus plant named 'Sunsenedibu' differs from similar varieties, 'Miss Yokohama', and 'Midget', and parental varieties, *Senecio heritierii* and 'Jupiter Blue', in the following botanical characteristics.

1. 'Sunsenedibu' is a high type plant, 34 cm in height. 'Miss Yokohama' is a compact type plant, 19 cm in height. 'Midget' is a compact type plant, 14 cm in height. The pollen parent *Senecio heritierii* is a semi-compact type plant, 26 cm in height, and female parent 'Jupiter Blue' is a compact type plant, 18.5 cm in height.

2. The flower of 'Sunsenedibu' has deep violet petals, deep violet disk flowers and no marginal variegation. That of 'Miss Yokohama' has vivid violet petals, deep violet disk flowers and white marginal parts. That of 'Midget' has vivid reddish purple petals, strong reddish purple disk flowers and no marginal variegation. That of female parent 'Jupiter Blue' has vivid blue petals, deep blue disk flowers and no marginal variegation. That of pollen parent *Senecio heritierii* has strong purple petals, strong reddish purple disk flowers and white marginal parts.

3. The leaf of 'Sunsenedibu' is smaller than that of 'Miss Yokohama' or 'Midget'.

4. 'Sunsenedibu' has fewer pubescence of stems than that of 'Miss Yokohama' or 'Midget'.

5. The blooming term of 'Sunsenedibu' is longer than that of 'Miss Yokohama' or 'Midget'.

6. The fertility of 'Sunsenedibu' is lower than that of 'Miss Yokohama' or 'Midget'.

Plant height, flower color and leaf size are the most distinctive characteristics of this new variety 'Sunsenedibu'.

DESCRIPTION OF THE VARIETY

Figure 1:
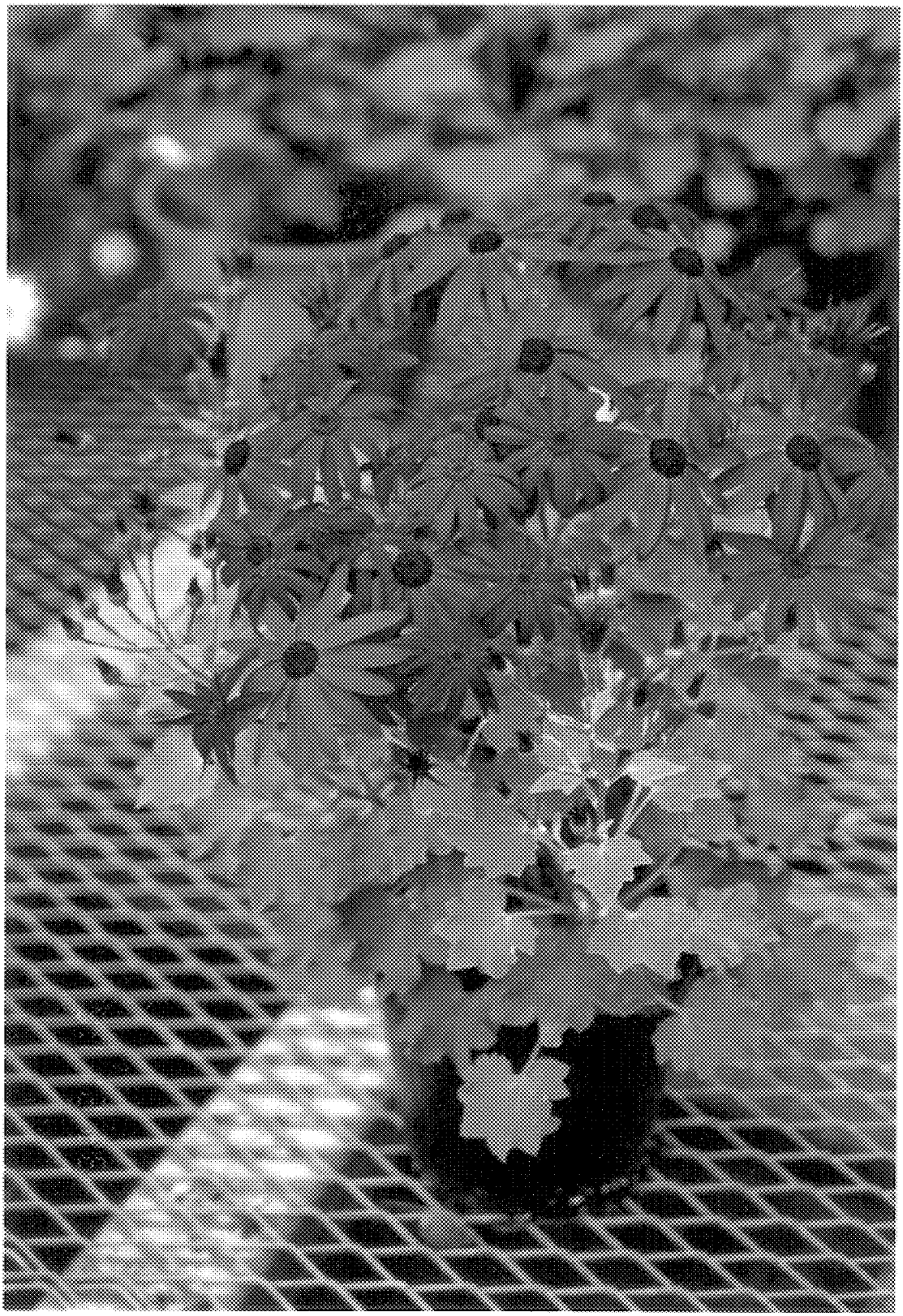
FIG. 1 is a photograph giving a partial view of the new variety of Senecio genus plant named 'Sunsenedibu' planted in a pot.
Figure 2:
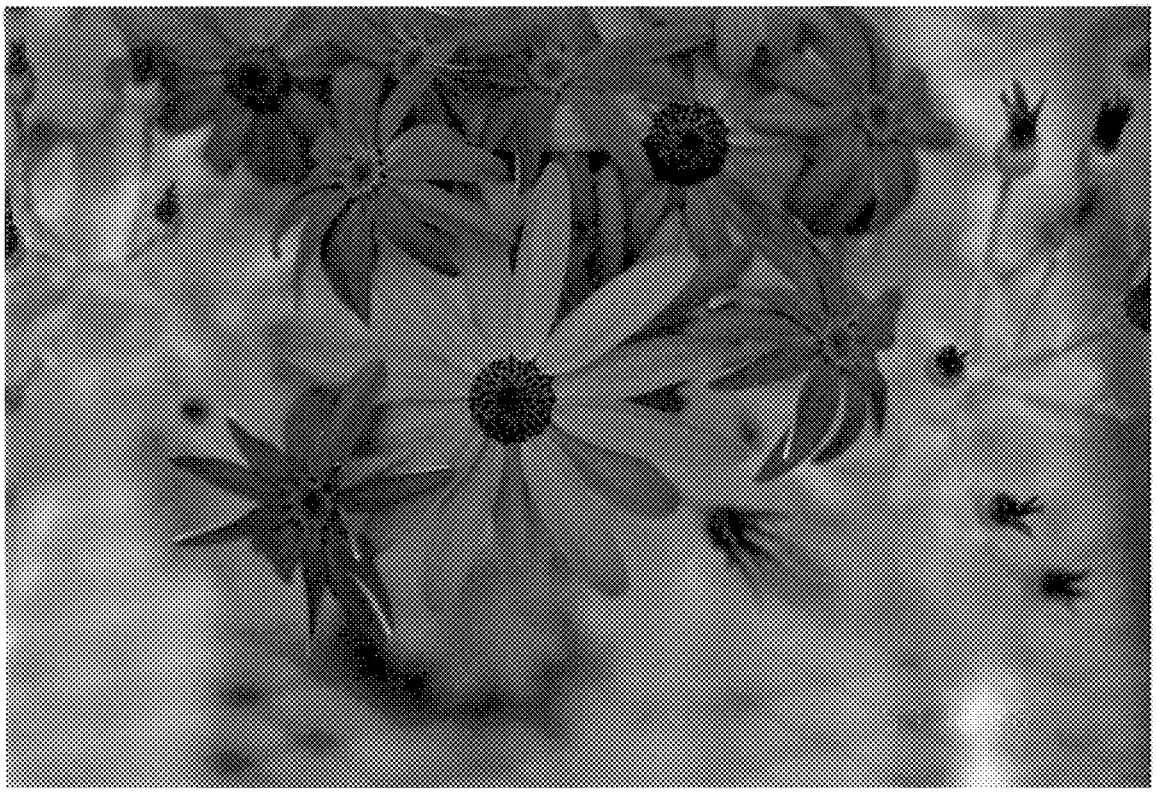
FIG. 2 is a photograph of flowers of the new variety of Senecio genus plant named 'Sunsenedibu'.

The botanical characteristics of this new and distinct variety of Senecio genus plant named 'Sunsenedibu' are as follows based on observations made 6 months after cutting in July (observations made in the next January).

Plant:
- *Growth habit.*—Semi-dwarf erect.
- *Height.*—34 cm.

Stem:
- *Thickness.*—4.2 mm.
- *Color.*—R.H.S.C.C.No. 59B or 59D.
- *Anthocyanin coloration.*—A presence of anthocyanin results in a color of R.H.S.C.C.No. 59D.
- *Degree of anthocyanin coloration.*—Light (resulting in a color of R.H.S.C.C.No. 59D.
- *Branching.*—Abundant, 9 to 11 branches.
- *Type of primary lateral shoot.*—Branch from every node.
- *Pubescence.*—Sparse.
- *Length of internode.*—1.1 cm.

Leaf:
- *Whole shape.*—Heart form with a swollen basal part, which is notched at where the basal part attaches to a petiole.
- *Depth of concavity of leaf margin.*—Deep (the distance from the deepest depth of concavity of the leaf margin to the average peak height of convexity is 7 mm).
- *Type of convexity.*—Acute, i.e. pointed serrations in the leaf margin.
- *Apex shape.*—Acute.
- *Base shape.*—Cordate.
- *Degree of undulation.*—Strong.
- *Length.*—7.0 cm.
- *Width.*—7.7 cm.
- *Diameter of petiole.*—3.0 mm.
- *Length of petiole.*—7.8 cm.
- *Color of petiole.*—R.H.S.C.C.No. 59B at the base (i.e. the part near the stem) and R.H.S.C.C.No. 138B at the end (i.e. the part near the blade).
- *Stipule.*—Absent.
- *Color of upper surface.*—Moderate yellowish green (R.H.S.C.C.No. 137C, J.H.S.C.C.No. 3712).
- *Color of reverse surface.*—Moderate yellowish green (R.H.S.C.C.No. 138C, J.H.S.C.C.No. 3709).
- *Anthocyanin coloration of reverse surface.*—Absent.
- *Pubescence of upper surface.*—Dense.
- *Pubescence of reverse surface.*—Dense.
- *Color of pubescence of reverse surface.*—White.

Flower (single flowered):
- *Shape of flower cluster.*—Uneven.
- *Diameter of flower cluster.*—30 cm.
- *Height of flower cluster.*—19 cm (i.e. the height of the upper most flower minus that of the lowest flower is 19 cm).
- *Transected shape of corolla.*—Reflex.
- *Diameter of flower.*—7.0 cm.
- *Size of disk flower.*—1.2 cm.
- *Color of petal.*—Deep violet (R.H.S.C.C.No. 93A, J.H.S.C.C.No. 8006) or R.H.S.C.C.No. 89B depending on the light condition.
- *Marginal variegation.*—Absent.
- *Color of disk flower.*—Deep violet (R.H.S.C.C.No. 93A, J.H.S.C.C.No. 8006) or R.H.S.C.C.No. 89A (at the center of the disk, not of the pistil, before the blooming of the tubular floret).
- *Petal length.*—2.9 cm.
- *Petal width.*—0.8 cm.
- *Shape of petal.*—Rectangular.
- *Lengthwise warp of petal.*—Flat.
- *Concavity of petal tip.*—Present.

*Shape of petal tip.*—Acute.
*Number of ray flower.*—13.
*Number of disk flower.*—158.
*Diameter of pedicel of the first flower in a blooming period (the flower is attached to the top of a main stem).*—0.9 mm.
*Length of pedicel of the first flower in a blooming period (the flower is attached to the top of a main stem).*—5.6 cm.
*Number of flowers per flower cluster.*—120.
*Scent.*—Present.

Calyx:
*Degree of concavity.*—Concave.
*Degree of recurvature.*—1.6 mm.
*Color.*—Very pale green (R.H.S.C.C.No. 130D, J.H.S.C.C.No. 4302) or R.H.S.C.C.No. 59D (in the presence of anthocyanin).
*Anthocyanin coloration.*—Present (the presence of anthocyanin results in R.H.S.C.C.No. 59D).

Pistil:
*Color.*—Deep violet (R.H.S.C.C.No. 93A, J.H.S.C. C.No. 8006).
*Number.*—1.
*Type.*—The top of the style is separated into two and the shape of the top is truncated.

Stamen:
*Color.*—Deep violet (R.H.S.C.C.No. 93A, J.H.S.C. C.No. 8006).
*Type.*—5 anthers are connate, with separated filaments.
*Blooming period.*—Beginning of December (Cutting in July).

Hardiness:
*Cold.*—Good.
*Heat.*—Good.

Resistance:
*Disease.*—Good.
*Insect.*—Good.

The new variety and *Senecio cruentus* have similar resistance to diseases (e.g. powdery mildew and leaf spot) and insects (aphid, while fly and trips). The new variety of Senecio genus plant named 'Sunsenedibu' is a tall plant most suitable for flower potting.

This new and distinct variety of Senecio genus plant named 'Sunsenedibu' was asexually reproduced by cutting at Hakushu-cho, Kitakoma-gun, Yamanashi-ken, Japan and the homogeneity and stability thereof were confirmed.

I claim:

1. A new and distinct variety of Senecio genus plant named 'Sunsenedibu', substantially as herein illustrated and described, characterized particularly by (A) being a high and dome-shaped plant with abundant branching, (B) having very few pubescences on its stems, (C) having small leaves, (D) having a large flower cluster with large flowers, (E) having deep violet petals and disk flowers, (F) having flowers with no marginal variegation, (G) having a long blooming term and (H) having low fertility.

* * * * *